United States Patent
Lin et al.

(10) Patent No.: US 10,933,107 B2
(45) Date of Patent: Mar. 2, 2021

(54) COMPOSITION COMPRISING PLANT EXTRACT AND USE THEREOF

(71) Applicant: TCI CO., LTD, Taipei (TW)

(72) Inventors: Yung-Hsiang Lin, Taipei (TW); I-Hui Chen, Taipei (TW); Kai-Wen Kan, Taipei (TW); Fu Chen Liu, Taipei (TW); Ciao-Ting Chen, Taipei (TW)

(73) Assignee: TCI CO., LTD., Taipei (TW)

( * ) Notice: Subject to any disclaimer, the term of this patent is extended or adjusted under 35 U.S.C. 154(b) by 2 days.

(21) Appl. No.: 16/499,473

(22) PCT Filed: Apr. 3, 2018

(86) PCT No.: PCT/CN2018/081717
§ 371 (c)(1),
(2) Date: Sep. 30, 2019

(87) PCT Pub. No.: WO2018/184525
PCT Pub. Date: Oct. 11, 2018

(65) Prior Publication Data
US 2020/0054705 A1 Feb. 20, 2020

Related U.S. Application Data

(60) Provisional application No. 62/503,185, filed on May 8, 2017, provisional application No. 62/480,860, filed on Apr. 3, 2017.

(51) Int. Cl.

| | | |
|---|---|---|
| A61K 36/00 | (2006.01) |
| A61K 36/185 | (2006.01) |
| A23L 33/105 | (2016.01) |
| A61K 9/00 | (2006.01) |
| A61K 9/08 | (2006.01) |
| A61K 9/48 | (2006.01) |
| A61P 3/04 | (2006.01) |
| A61K 31/01 | (2006.01) |
| A61K 31/015 | (2006.01) |
| A61K 36/21 | (2006.01) |
| A61K 36/258 | (2006.01) |
| A61K 36/31 | (2006.01) |
| A61K 36/45 | (2006.01) |
| A61K 36/48 | (2006.01) |
| A61K 36/53 | (2006.01) |
| A61K 36/67 | (2006.01) |
| A61K 36/73 | (2006.01) |
| A61K 36/74 | (2006.01) |
| A61K 36/752 | (2006.01) |
| A61K 36/815 | (2006.01) |
| A61K 36/82 | (2006.01) |
| A61K 36/87 | (2006.01) |
| A61K 36/886 | (2006.01) |
| A61K 36/8962 | (2006.01) |
| A61K 36/9066 | (2006.01) |
| A61K 8/9789 | (2017.01) |
| A61P 17/16 | (2006.01) |
| A61Q 19/00 | (2006.01) |
| A23F 3/16 | (2006.01) |
| A61K 8/97 | (2017.01) |
| A61Q 17/04 | (2006.01) |
| A61P 19/04 | (2006.01) |
| A61Q 19/08 | (2006.01) |

(52) U.S. Cl.
CPC ............ *A61K 36/185* (2013.01); *A23F 3/163* (2013.01); *A23L 33/105* (2016.08); *A61K 8/97* (2013.01); *A61K 8/9789* (2017.08); *A61K 9/0056* (2013.01); *A61K 9/0095* (2013.01); *A61K 9/08* (2013.01); *A61K 9/48* (2013.01); *A61K 31/01* (2013.01); *A61K 31/015* (2013.01); *A61K 36/21* (2013.01); *A61K 36/258* (2013.01); *A61K 36/31* (2013.01); *A61K 36/45* (2013.01); *A61K 36/48* (2013.01); *A61K 36/53* (2013.01); *A61K 36/67* (2013.01); *A61K 36/73* (2013.01); *A61K 36/74* (2013.01); *A61K 36/752* (2013.01); *A61K 36/815* (2013.01); *A61K 36/82* (2013.01); *A61K 36/87* (2013.01); *A61K 36/886* (2013.01); *A61K 36/8962* (2013.01); *A61K 36/9066* (2013.01); *A61P 3/04* (2018.01); *A61P 17/16* (2018.01); *A61P 19/04* (2018.01); *A61Q 17/04* (2013.01); *A61Q 19/007* (2013.01); *A61Q 19/08* (2013.01); *A23V 2002/00* (2013.01)

(58) Field of Classification Search
CPC ...................................................... A61K 36/00
USPC ......................................................... 424/725
See application file for complete search history.

(56) References Cited

FOREIGN PATENT DOCUMENTS

| | | |
|---|---|---|
| CN | 101674821 A | 3/2010 |
| CN | 102132872 A | 7/2011 |
| CN | 105941728 A | 9/2016 |

OTHER PUBLICATIONS

The Government of India, the Biological Diversity Act, 2002.
Hu Yang, "Molecular Regulation of Glucose Transportt System", Beijing Sport University Press, Mar. 31, 2013, pp. 191-192, (Exercise Molecular Biology).
Examination report dated Nov. 20, 2020, listed in correspondent Taiwan patent application No. 107111697 (publication No. TW201836631).

*Primary Examiner* — Michael V Meller
(74) *Attorney, Agent, or Firm* — Chieh-Mei Wang

(57) ABSTRACT

Provided is a composition comprising a plant extract. The plant extract includes a citrus extract and a green tea extract. The extract combination can effectively increase expression of GLUT4 gene.

4 Claims, 1 Drawing Sheet
Specification includes a Sequence Listing.

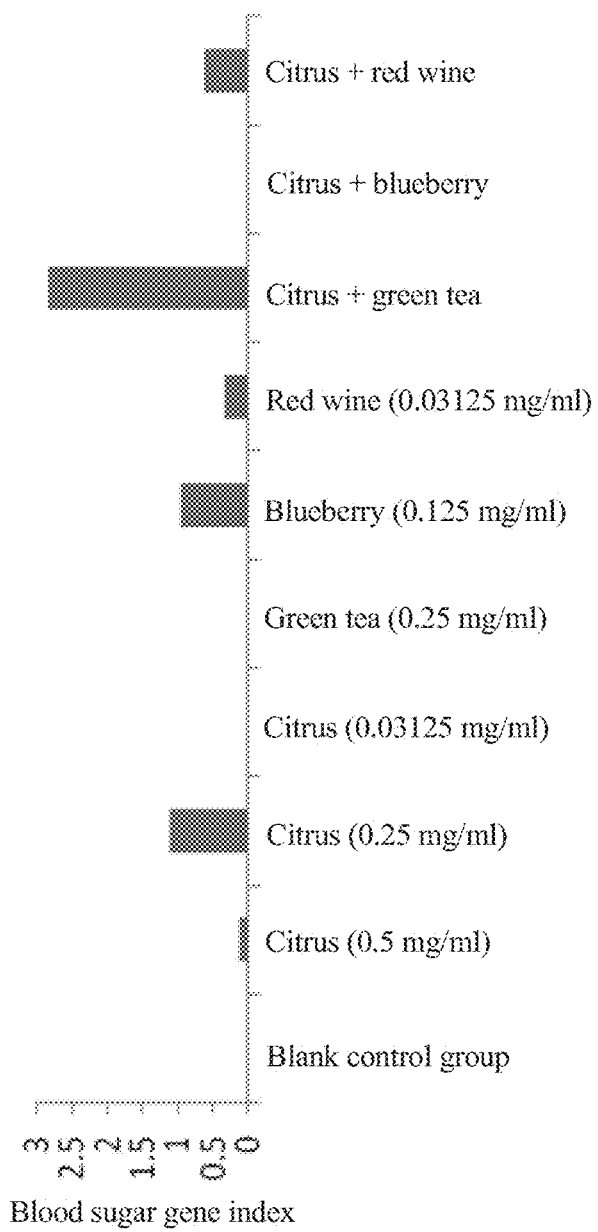

COMPOSITION COMPRISING PLANT EXTRACT AND USE THEREOF

CROSS-REFERENCE TO RELATED APPLICATION

This application claims priority of U.S. patent application No. 62/480,860, filed on Apr. 3, 2017, and U.S. patent application No. 62/503,185, filed on May 8, 2017, the content of which is incorporated herein in its entirety by reference.

BACKGROUND OF THE INVENTION

1. Field of the Invention

The present invention relates to a composition comprising a plant extract and use thereof, in particular to a composition for promoting expression of the GLUT4 gene, regulating blood sugar, and uses thereof.

2. The Prior Art

Blood sugar refers to glucose in the blood, which is derived from the digestion of the small intestine and can be further transported by blood to various cells in the body as the main source of energy for the cells. In humans, the concentration of blood sugar is strictly regulated and controlled. The general concentration is about 900 mg/L (i.e., 5 mmol/L or 90 mg/dl), and the normal range is between 4-6 mmol/L. The concentration of blood sugar is maintained in a constant concentration range, but with diet and rest, there will be large fluctuations. Generally, one to two hours after eating, blood sugar concentration will rise, and in the morning will be minimized Deregulation of blood sugar levels can lead to a variety of diseases (e.g., diabetes), especially when persistent blood sugar levels are too high.

Diabetes can be classified into type 1 diabetes, in which insulin cannot produce or produce insufficient, and type 2 diabetes, in which cells respond abnormally or unresponsive to insulin. Regardless of the type of diabetes, if left untreated, it will cause many complications, such as: diabetic ketoacidosis, hyperglycemic hyperosmolar nonketotic coma, and cardiovascular disease, chronic kidney disease, retinopathy, diabetic foot, strokes, etc. According to statistics, there are about 422 million people with diabetes in the world in 2016. Many patients suffer from complications, their quality of life declines, and their life risks are even higher. Therefore, the regulation of blood sugar has always been the goal that scientists are trying to solve.

Glucose transporter 4 (GLUT4), which is involved in the transport of glucose, is mainly found in muscle and cartilage tissue. When the protein is in the cytoplasm, it can bind to insulin. Once the blood sugar level is increased, it will stimulate GLUT4 to move to the cell membrane, releasing insulin to rapidly regulate blood sugar, and can also bind glucose to carry it back into the cell. Therefore, if the gene expression of GLUT4 can be increased, more GLUT4 will be produced, and the sensitivity to insulin can be improved to achieve the purpose of adjusting or lowering blood sugar.

Among the plants or health-care ingredients that people often eat or drink, such as: red wine, citrus, blueberries, and green tea, etc. It is unknown whether the above components alone or in combination have the effect of promoting expression of the GLUT4 gene. If a combination of components that can significantly increase the expression of the GLUT4 gene can be found from the complex composition, it will be good news for the diabetic patients.

SUMMARY OF THE INVENTION

A primary objective of the present invention is to provide a composition comprising a plant extract. By itself or as a pharmaceutical composition or a food composition, which can combine the effects of extracts and/or other components of various plants to significantly promote the expression of the GLUT4 gene, thereby achieving the purpose of allowing individuals to achieve moderate adjustment or reduction in blood sugar concentration.

According to an embodiment of the present invention, the composition comprises a citrus extract and a green tea extract.

According to an embodiment of the present invention, a ratio of the citrus extract to the green tea extract is 0.8-1.2:1.2-0.8, preferably 1:1.

According to an embodiment of the present invention, each of the citrus extract and the green tea extract is in a range of 0.03125-0.25 mg/ml.

Another objective of the present invention is to provide a pharmaceutical composition for promoting the expression of the GLUT4 gene, comprising the aforementioned composition and a pharmaceutically acceptable carrier.

According to an embodiment of the present invention, the pharmaceutical composition is in a form of a solution, a capsule or a lozenge.

Another objective of the present invention is to provide a food composition for promoting the expression of the GLUT4 gene.

According to an embodiment of the present invention, the food composition comprises the aforementioned composition and a food ingredient, wherein the food ingredient is a component of a general food, a health food, a dietary supplement or a drink.

Another objective of the present invention is to provide a method for promoting expression of the GLUT4 gene, comprising administering to a subject in need thereof an effective amount of the aforementioned composition.

According to an embodiment of the present invention, the composition is a pharmaceutical composition for promoting expression of the GLUT4 gene.

According to an embodiment of the present invention, the composition is a food product, a health food, a dietary supplement or a drink for promoting expression of the GLUT4 gene.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

FIG. 1 is a diagram comparing the effects of different plant extracts or combinations on GLUT4 gene expression in an embodiment of the present invention.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Example 1

Preparation of Green Tea Extract

First, the green tea leaves were washed and dried, and the green tea leaves were coarsely crushed by a pulverizer. Water was used as a solvent, and the solvent and the resultant crude green tea were mixed at a liquid-solid ratio of 5-20:1-5. After that, the crude green tea was extracted at 50° C. to 100° C. for 0.5 to 3 hours. The extraction temperature is preferably from 75° C. to 95° C.

After the green tea extract obtained by the above extraction step was cooled to room temperature, it was filtered through a strainer of 400 mesh to remove residual solids. The filtered green tea extract can be further concentrated under reduced pressure at 45° C. to 70° C. to obtain a concentrated product.

Example 2

Preparation or Source of Other Plant Extracts

The citrus extract of the examples of the present invention was obtained by extracting *Citrus reticulata* fruit, which was commercially available from LAWTON Trading Co., Ltd. The red wine extract was obtained by extracting red wine, which was commercially available from Shanghai Boyoutang Biotechnology Co., Ltd. The green coffee bean extract was obtained by extracting seeds of unroasted *Coffea* spp., which was commercially available from ARJUNA NATURAL EXTRACTS Ltd. (India). The blueberry extract was obtained by extracting the *Vaccinium Cyanococcus* fruit, which was commercially available from Biomed Herbal Research Co., Ltd. These extracts are formulated in water at appropriate concentrations for use.

Example 3

Detection of Blood Sugar Regulating Genes

HepG2 cells (purchased from ATCC HB8065) were prepared and cultured in a cell culture medium (Dulbecco's modified Eagle's medium (Gibco) containing 1% penicillin/streptomycin and 10% fetal bovine serum). 2 ml of the cell culture medium was added to each well of a 6-well plate to have $1.5 \times 10^5$ HepG2 cells per well.

The samples were then divided into two groups, of which group A was the blank control group, and group B was the test group. In group B, according to the plant extracts and component types listed in Table 1, at doses of 0.03125 mg/ml to 0.5 mg/ml, single extract prepared in Example 1 or Example 2 or combination of two extracts prepared in Example 1 or Example 2 in a ratio of 1:1 were added, and then reacted at 37° C. for 6 and 24 hours. After that, the expression of the GLUT4 gene was analyzed. The doses shown in the tables are the doses of the single extract, or the components of the combination extract.

Cells in each of the above groups were recovered, RNA was extracted with an RNA extraction kit (Genemark), and the RNA (2000 ng) was reverse-transcribed into cDNA by the reverse transcriptase (Superscript III Reverse Transcripatase, Invitrogen). Then, qPCR (KAPA CYBR FAST qPCR Kits, KAPA Biosystems) was performed using the primer pairs listed in Table 2 and the ABI Step One Plus Real-Time PCR system to quantify the expression of the GLUT4 gene (the expression of the ACTB (beta-actin) gene was used as an internal control group). During the real-time polymerase chain reaction, the melting curve was analyzed, and the SCORE method was used. The cycle threshold (Ct) of the aforementioned ACTB gene was used as the internal control group, and the blank control group was used as the control gene for relative quantitative analysis of gene expression. When analyzed by the SCORE method, the relative expression of mRNA of the target gene (GLUT4) was derived from the equation $2^{-\Delta Ct}$, wherein $\Delta Ct = C_{target\ gene} - Ct_{ACTB}$, and then the difference between the expression level of GLUT4 gene in each group and the blank control group was calculated. The sum of the differences was used as the blood sugar gene index. The blood sugar gene index corresponding to gene expression is shown in Table 1 and FIG. 1, and FIG. 1 is a histogram graphically shown in Table 1. The higher the index value, the better the promotion of GLUT4 gene expression.

TABLE 1

| Plant extract/composition | dose/ratio | blood sugar gene index |
|---|---|---|
| blank control group | 0 | 0 |
| citrus | 0.5 mg/ml | 0.13 |
| citrus | 0.25 mg/ml | 1.10 |
| citrus | 0.03125 mg/ml | 0 |
| green tea | 0.25 mg/ml | 0 |
| blueberry | 0.125 mg/ml | 0.96 |
| red wine | 0.03125 mg/ml | 0.33 |

TABLE 1-continued

| Plant extract/composition | dose/ratio | blood sugar gene index |
|---|---|---|
| citrus + green tea | 0.25 mg/ml (1:1) | 2.84 |
| citrus + blueberry | 0.5 mg/ml (1:1) | 0 |
| citrus + red wine | 0.03125 mg/ml (1:1) | 0.61 |

TABLE 2

| Gene | Primer | SEQ ID NO | Primer length (ntds) | Product length (ntds) |
|---|---|---|---|---|
| GLUT4 | GLUT4-F | SEQ ID NO: 1 | 18 | 200 |
|  | GLUT4 -R | SEQ ID NO: 2 | 24 |  |

From the results of Table 1 and FIG. 1, the index of the promoting effect of the citrus extract alone (0.25 mg/ml) on GLUT4 gene expression was 1.10, and the index of promoting effect of the green tea extract alone (0.25 mg/ml) was 0. However, when the two were combined, the index of the promoting effect can be as high as 2.84, which was greatly increased to 258% compared with that of the citrus extract alone. In contrast, if the citrus extract was combined with the blueberry extract, the index of the promoting effect was reduced to 0. Therefore, the effect of the combination between the extracts is not necessarily the synergistic effect. In the examples of the present invention, the promoting effect obtained by combining the citrus extract with the green tea extract is preferred.

It can be seen from the above test that the composition for promoting GLUT4 gene expression in the embodiment of the present invention, when combined with the two extracts of the citrus extract and the green tea extract, can produce an unexpected synergistic effect, so that the expression of GLUT4 gene is increased significantly. Accordingly, these compositions can be utilized to prepare related pharmaceutical or food compositions that allow the applicator or consumer to achieve an adjustment in blood sugar concentration, thereby improving hyperglycemia.

Further, the composition having the function of promoting GLUT4 gene expression according to an embodiment of the present invention may be further added to a food, a health food, a dietary supplement or a drink. When the composition having the function of promoting GLUT4 gene expression according to an embodiment of the present invention is prepared as a pharmaceutical composition, the pharmaceutical composition may be further added to a carrier or other adjuvants well known in the art. The dosage form of the pharmaceutical composition can be, but is not limited to, a solution, a capsule, or a lozenge.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method of treating diabetes in a human in need thereof consisting essentially of administering synergistically effective amounts of a mandarin orange extract and a green tea extract to the human in need thereof to effectively treat the diabetes in the human in need thereof.

2. The method of claim 1, wherein the synergistically effective amounts are in a ratio of the mandarin orange extract to the green tea extract of 0.8-1.2:1.2-0.8.

3. The method of claim 2, wherein the synergistically effective amounts are in a ratio of the mandarin orange extract to the green tea extract of 1:1.

4. The method of claim 1, wherein the synergistically effective amounts of the mandarin orange extract and the green tea extract are in a range of 0.03125-0.25 mg/ml.

* * * * *

SEQUENCE LISTING

```
<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: forward primer for PCR

<400> SEQUENCE: 1
aggctgggcc gatgtttc                                                 18

<210> SEQ ID NO 2
<211> LENGTH: 24
<212> TYPE: DNA
<213> ORGANISM: Artificial Sequence
<220> FEATURE:
<223> OTHER INFORMATION: reverse primer for PCR

<400> SEQUENCE: 2
cgaagatgct ggtcgaataa taga                                          24
```